US009801970B2

(12) United States Patent
Chase et al.

(10) Patent No.: US 9,801,970 B2
(45) Date of Patent: Oct. 31, 2017

(54) DECORATIVE FRAGRANCE DISPENSING SYSTEM

(71) Applicant: SimpleScents Brands LLC, Draper, UT (US)

(72) Inventors: Benjamin R Chase, Highland, UT (US); David Hendrickson, West Valley, UT (US)

(73) Assignee: Ambrosia Corporation, Guaynabo, PR (US)

( * ) Notice: Subject to any disclaimer, the term of this patent is extended or adjusted under 35 U.S.C. 154(b) by 288 days.

(21) Appl. No.: 14/517,776

(22) Filed: Oct. 17, 2014

(65) Prior Publication Data

US 2015/0108240 A1     Apr. 23, 2015

Related U.S. Application Data

(60) Provisional application No. 61/893,021, filed on Oct. 18, 2013.

(51) Int. Cl.
   *A61L 9/12*              (2006.01)
   *A61L 9/04*              (2006.01)

(52) U.S. Cl.
   CPC ............... *A61L 9/122* (2013.01); *A61L 9/04* (2013.01); *A61L 9/12* (2013.01); *A61L 2209/12* (2013.01)

(58) Field of Classification Search
   CPC ....................................... A61L 9/122
   USPC ....................................... 422/124
   See application file for complete search history.

(56) References Cited

U.S. PATENT DOCUMENTS

| | | | | |
|---|---|---|---|---|
| 5,087,273 A * | 2/1992 | Ward | ...................... | B01D 39/00 239/55 |
| 5,433,923 A * | 7/1995 | Wolverton | .............. | A61L 9/037 422/121 |
| 6,050,551 A * | 4/2000 | Anderson | ............... | A61L 9/122 239/56 |
| 6,425,527 B1 * | 7/2002 | Smole | ....................... | F24F 7/00 236/49.3 |
| 6,719,217 B1 * | 4/2004 | Tawara | .................. | A61L 9/122 239/302 |

(Continued)

FOREIGN PATENT DOCUMENTS

CA          2290177 A1 *    4/2001

OTHER PUBLICATIONS

English translation of Doc. No. CA 2290177 A1 provided by Thomson Reuters : Derwent Doc. No. 2001-425935 "Air purifying filter includes fan drawing air over carbon filter and semi-solid gel to remove odors".*

(Continued)

*Primary Examiner* — Kevin Joyner
*Assistant Examiner* — Holly Mull
(74) *Attorney, Agent, or Firm* — Christopher G. Darrow; Darrow Mustafa PC

(57) ABSTRACT

A fragrance dispensing apparatus includes a housing. The housing includes a platform configured to receive an ethylene vinyl acetate (EVA) bead packet. The EVA bead packet remains substantially unheated by the fragrance dispensing apparatus during operation of the fragrance dispensing apparatus. The fragrance dispensing apparatus further includes a lower module. The lower module includes a fan configured to selectively actuate airflow through the EVA bead packet.

19 Claims, 11 Drawing Sheets

(56) References Cited

U.S. PATENT DOCUMENTS

| | | | |
|---|---|---|---|
| 6,790,003 B1* | 9/2004 | Hu | F04D 25/0613 |
| | | | 415/118 |
| 6,913,733 B2 | 7/2005 | Hardy et al. | |
| 7,093,949 B2 | 8/2006 | Hart et al. | |
| 7,455,245 B2 | 11/2008 | Sipinski et al. | |
| 7,637,737 B2 | 12/2009 | Furner et al. | |
| 7,931,213 B2 | 4/2011 | Ousley | |
| 8,369,694 B2 | 2/2013 | Pitz et al. | |
| 8,412,029 B2 | 4/2013 | Browder et al. | |
| 8,480,248 B2 | 7/2013 | Demarest et al. | |
| 9,474,818 B1* | 10/2016 | Shotey | A61L 9/032 |
| 2005/0053493 A1* | 3/2005 | Chung | F04D 29/384 |
| | | | 417/423.3 |
| 2005/0084413 A1 | 4/2005 | Stanley, III | |
| 2006/0120080 A1 | 6/2006 | Sipinski et al. | |
| 2008/0127820 A1* | 6/2008 | Park | A61L 9/122 |
| | | | 95/1 |
| 2008/0130266 A1 | 6/2008 | DeWitt et al. | |
| 2009/0134239 A1 | 5/2009 | Neumann | |
| 2011/0148329 A1* | 6/2011 | Demarest | A01M 1/2033 |
| | | | 315/313 |
| 2013/0068788 A1* | 3/2013 | Gasper | A01M 1/2038 |
| | | | 222/63 |
| 2014/0369895 A1* | 12/2014 | Turner | A61L 9/122 |
| | | | 422/124 |

OTHER PUBLICATIONS

NCR18650A Specification Sheet, Panasonic, 2012.*

* cited by examiner

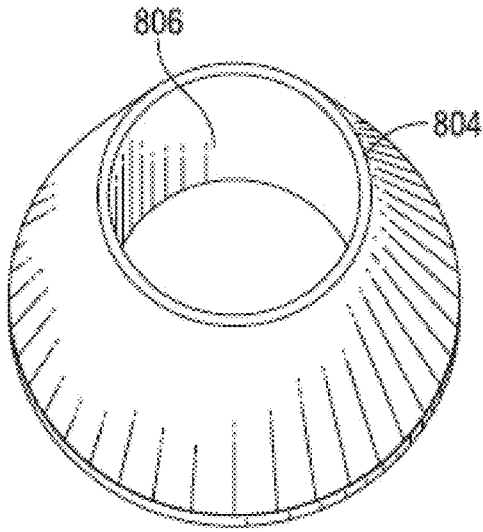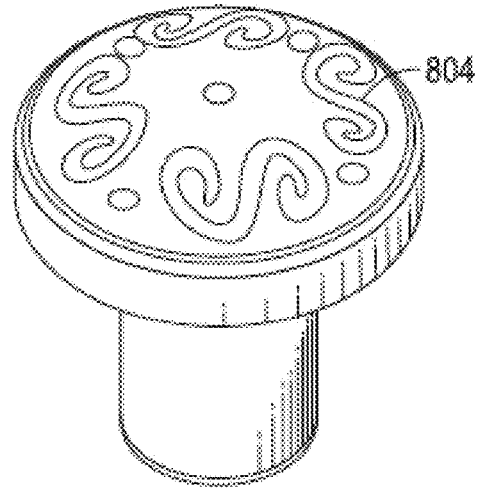
FIG. 10A     FIG. 10B
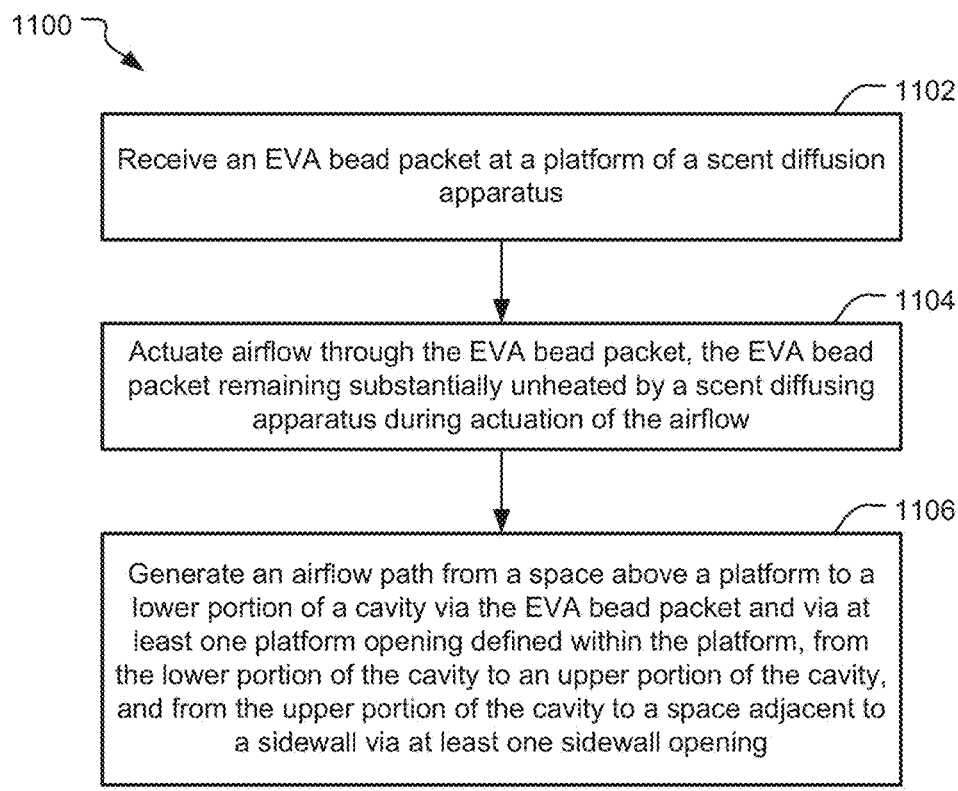
FIG. 11

DECORATIVE FRAGRANCE DISPENSING SYSTEM

RELATED APPLICATIONS

This application claims the benefit, under 35 U.S.C. §119, of U.S. Provisional Patent Application Ser. No. 61/893,021 filed on Oct. 18, 2013, and entitled "Decorative Fragrance Dispensing System," which is hereby incorporated by reference in its entirety.

FIELD OF THE DISCLOSURE

This disclosure generally relates to a decorative fragrance dispensing system.

BACKGROUND

Fragrance dispensing products may be used to dispense fragrance into surrounding air (for example, within a room, office, workplace, or household), thereby "freshening" the air and creating a pleasant atmosphere. In creating the pleasant atmosphere, ambient lighting may also be included as part of a fragrance dispensing product. Examples of types of fragrance dispensing products may include candles, air fresheners, electric fragrance dispensers, etc.

Some fragrance dispensing products use fragrance elements such as melted wax, gels, and/or liquids, to hold and dispense fragrance. These products may become messy if the wax, gels, or liquids are spilled. Further, children and/or animals may be inclined to play with or eat the wax, gels, or liquids. Hence, current fragrance dispensing systems may present a danger to children and/or animals.

Some products may use molded EVA plastic infused with fragrance instead of wax, gels, or liquids. However, such products use heating elements to heat the EVA plastic to temperatures between about 100° F. and 150° F. The heat causes the EVA plastic to release the fragrance. Using a heating element within a fragrance dispensing system may be dangerous to people or articles that may come in contact with the heating element or a heated portion of the fragrance dispensing system. Further, using molded plastics may not enable sufficient airflow to pass through the fragrance dispensing system to infuse the air with the fragrance.

SUMMARY

Disclosed is a portable and decorative system that distributes fragrance into a large area without using heat. The disclosed system may resolve or mitigate at least one disadvantage of current systems described above and or one or more additional disadvantages known in the relevant art. The system may produce light and spread the fragrance by means of a battery operated fan module and a fragrance packet. The system may be powered by a low voltage and low power consumption rechargeable battery that is part of a module assembly. The low voltage and low power consumption rechargeable battery may be recharged using a recharge cable that plugs into a wall outlet. The fragrance packet may be filled with ethylene vinyl acetate (EVA) that is infused with fragrance. The module may include a controller circuit (e.g., formed on a PCB) that operates one or more LED lights. Light from the LED lights may pass through openings in a housing of the system to provide ambient lighting. The outer housing may be made of different materials including ceramic, poly resin, wax or other materials, shapes and sizes. The module may be interchangeable between any of a plurality of outer housings. The controller circuit may also operate a fan that pulls fragrance from the top openings of the decorative outer housing and circulates it down and out of side openings defined within the housing. The controller circuit may also operate a timer and a power save mode feature that enables power conservation.

In an embodiment, a fragrance dispensing apparatus includes a housing. The housing includes a platform configured to receive an ethylene vinyl acetate (EVA) bead packet. The EVA bead packet remains substantially unheated by the fragrance dispensing apparatus during operation of the fragrance dispensing apparatus. The apparatus further includes a lower module. The lower module includes a fan configured to selectively actuate airflow through the EVA bead packet.

In an embodiment, the housing further includes a sidewall coupled to the platform. The sidewall and the platform may define a cavity. The platform may include at least one platform opening defined therein. The at least one platform opening may communicatively couple the cavity to a space above the platform. The sidewall may include at least one sidewall opening defined therein. The at least one sidewall opening may communicatively couple an upper portion of the cavity to a space adjacent to the sidewall.

In an embodiment, the fan may be further configured to generate an airflow path from the space above the platform to a lower portion of the cavity via the EVA bead packet and via the at least one platform opening, from the lower portion of the cavity to an upper portion of the cavity, and from the upper portion of the cavity to the space adjacent to the sidewall via the at least one sidewall opening. The fan may include three blades. Alternatively, the fan may include two diametrically opposed blades. An angle of the diametrically opposed blades may reduce a noise emitted by the fan while increasing an airflow through the housing. The fan may be transparent. The fragrance dispensing apparatus may further include a motor coupled to the fan. The motor may include cloth brushing.

In an embodiment, the fragrance dispensing apparatus further includes a rechargeable battery. The rechargeable battery may be a high capacity lithium-ion battery capable of operating the fan for at least 80 hours. Alternatively, the rechargeable battery may be a lower capacity battery. The fragrance dispensing apparatus may further include a recharging cable configured to be electrically coupled to the battery.

In an embodiment, the lower module further includes a twist locking mechanism that couples the lower module to the housing when enabled and that releases the housing when disabled. The housing may be configured to be removed and replaced by a second housing including a second platform configured to receive the EVA bead packet. The twist locking mechanism may include at least one notch attached to a side of the lower module.

In an embodiment, the lower module further includes at least one light emitting diode (LED) configured to illuminate inside the housing and shine through the at least on platform opening, the at least one sidewall opening, or both. The at least one LED may include six LEDs. The lower module may include a translucent plate separating the six LEDs from a cavity defined within the housing.

In an embodiment, the lower module further comprises a switch connector configured to receive a turnable knob. The housing may include ceramic, glass, poly resin, plastic, wood, or a combination thereof. The housing may be further configured to receive a topper including at least one topper opening defined therein. The topper and the platform form an upper cavity configured to retain the EVA bead packet.

In an embodiment, a method of dispensing fragrance includes receiving an EVA bead packet at a platform of a fragrance dispensing apparatus. The method further includes actuating airflow through the EVA bead packet. The EVA bead packet remains substantially unheated by the fragrance dispensing apparatus during actuation of the airflow.

In an embodiment, the method further includes generating an airflow path from a space above a platform to a lower portion of a cavity via the EVA bead packet and via at least one platform opening defined within the platform, from the lower portion of the cavity to an upper portion of the cavity, and from the upper portion of the cavity to a space adjacent to a sidewall via at least one sidewall opening.

In an embodiment, a fragrance dispensing apparatus includes one or more LEDs. The apparatus further includes a fan configured to actuate airflow through an EVA bead packet. The apparatus also includes a controller. The controller is configured to selectively enter an off state, a light only state, or an on state. The controller is further configured to refrain from operating the fan and the one or more LEDs while in the off state. The controller is also configured to refrain from operating the fan and operating the one or more LEDs while in the light only state. The controller is configured to operate the fan and operate the one or more LEDs while in the on state.

In an embodiment, the on state includes a low state and a high state. Operating the fan may include spinning the fan at a lower speed while in the low state than while in the high state. Operating the fan may include, while in a power saving state, performing power saving operations during 4 hours of a 24 hour period. The power saving operations may include operating the fan for a 15 minute period. The power saving operations may further include ceasing to operate the fan for a period of 5 minutes.

In an embodiment, the controller includes a printed circuit board (PCB). The PCB may be coupled to a four wire switch. The four wire switch may include an off position, a light only position, a low position, and a high position. The PCB may further be coupled to a power save switch. The power save switch may include an on position and an off position. The PCB may also be coupled to a processor configured to selectively operate the fan and the one or more LEDs based on a state of the four wire switch and a state of the power save switch.

BRIEF DESCRIPTION OF THE DRAWINGS

FIG. 10A is a diagram that depicts a lower view of an embodiment of a turnable knob;

FIG. 10B is a diagram that depicts an upper view of the embodiment of the turnable knob;

FIG. 11 is a flow chart that depicts of an embodiment of a method of fragrance dispensing;

Figure 1:
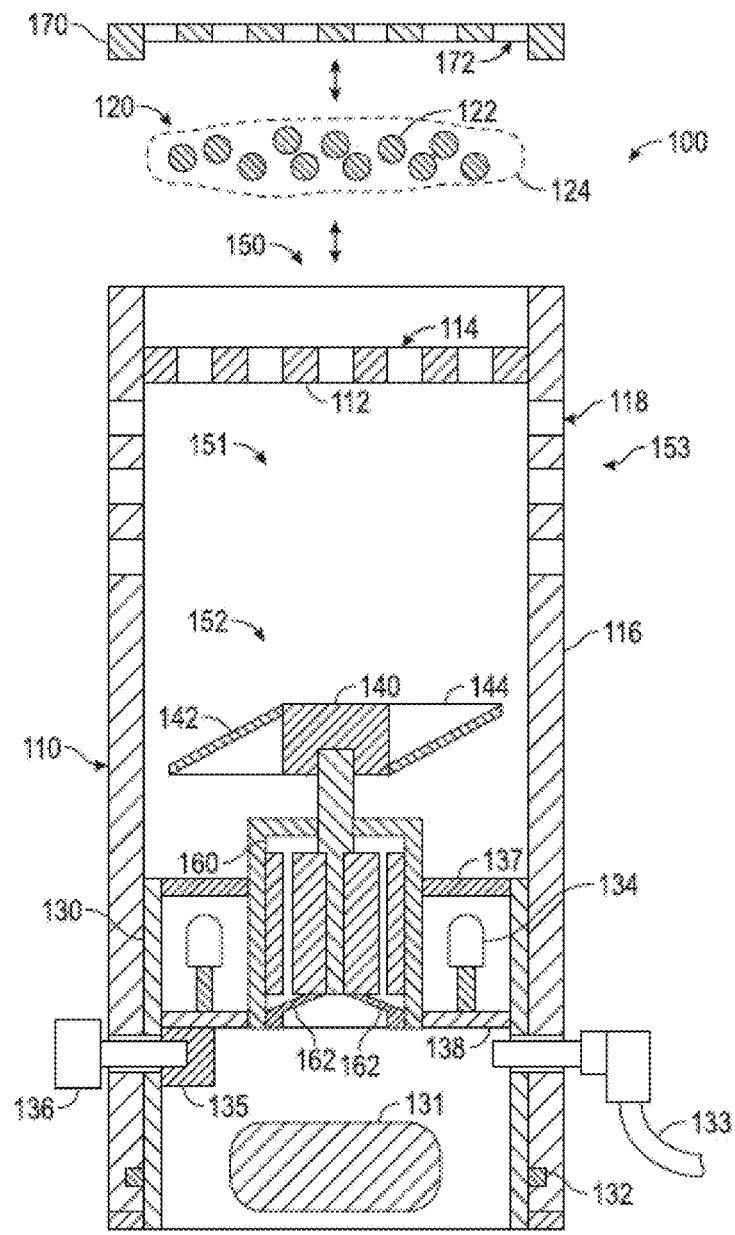
FIG. 1 is a diagram that depicts an embodiment of a fragrance dispensing system.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the spirit and scope of the invention as defined by the appended claims.

DETAILED DESCRIPTION

Referring to FIG. 1, an embodiment of a fragrance dispensing system is depicted and generally designated 100. The fragrance dispensing system 100 may include a housing 110, an ethylene vinyl acetate (EVA) bead packet 120, a lower module 130, and a fan 140. In some embodiments, the fragrance dispensing system 100 may also include a topper 170.

The housing 110 may include a platform 112 and a sidewall 116 coupled together such that the platform 112 and the sidewall 116 define a cavity that includes an upper portion 151 and a lower portion 152. Further, the platform 112 may include one or more openings, such as the opening 114 defined therein. The opening 114 may communicatively couple a space 150 above the platform 110 to the upper portion 151 of the cavity. For example, a change of air pressure within the upper portion of the cavity 151 may cause an airflow path to pass between the space 150 and the upper portion 151 of the cavity via the openings including the opening 114. Likewise, the sidewall 116 may include one or more openings, such as the opening 118 defined therein. The opening 118 may communicatively couple a space 153 adjacent to the sidewall 116 to the upper portion 151 of the cavity. The housing 110 may be formed from and include materials such as ceramic materials, poly resin materials, wax materials, etc. For example, the housing 110 may include ceramic, glass, poly resin, plastic, wood, metal, composites, another type of shapeable material, or a combination thereof.

The platform 112 may be configured to receive the EVA bead packet 120. For example, a size and/or a shape of the platform 112 may retain the EVA bead packet 120 when placed in contact with the EVA bead packet 120.

The EVA bead packet 120 may include a plurality of EVA beads such as the EVA bead 122 and a casing 124 enclosing the plurality of EVA beads. An embodiment of the EVA bead packet 120 is described further with reference to FIG. 12.

The lower module 130 may include a battery 131, a locking mechanism 132, a recharging cable 133, at least one light emitting diode (LED) 134, a switch connector 135, a turnable knob 136, a translucent plastic plate 137, and a controller circuit 138. Although not depicted in FIG. 1, the lower module 130 may include additional wires and circuitry coupling the elements of the lower module 130 together to enable various operations of the lower module 130 as described herein. The lower module 130 may be coupled to a fan 140 by a motor 160 to enable the motor and fan as described herein.

The battery 131 may include any battery capable of powering the motor 160 and the at least one LED 134. For example, the battery 131 may be a rechargeable high capacity lithium ion battery, such as a low voltage and power consumption DC 3.7 volt rechargeable lithium ion battery. The battery 131 may be electrically coupled to the motor 160 and the at least one LED 134 via the controller circuit 138 as described further with reference to FIG. 2. In an embodiment, the battery 131 may be capable of operating the fragrance dispensing system 100 as described herein for a period of at least 80 hours. In one or more other embodiments, the battery 131 may be a lower capacity battery and may be capable of operating the fragrance dispensing system 100 as described herein for a period of less than 80 hours.

The locking mechanism 132 may include any type of locking mechanism capable of coupling the housing 110 to the lower module 130 when enabled and releasing the housing 110 from the lower module 130 when disabled. In an embodiment, the locking mechanism 132 includes a twist locking mechanism. For example, the locking mechanism 132 may include a notch attached to a side of the lower module 130 as depicted in FIG. 1. The notch may be received by the housing 110. A particular embodiment of the locking mechanism is described further with reference to FIGS. 6A-7.

The recharging cable 133 may include any type of recharging cable capable of charging the battery 131. In an embodiment, the recharging cable 133 is electrically coupled to the battery 131 via the controller circuit 138 as described with reference to FIG. 2. The recharging cable 133 may further be configured to couple to an electrical outlet (e.g., a wall outlet) to receive power for recharging the battery 131. In an embodiment, the recharging cable 133 is a 1 amp 5 volt rechargeable cable.

The at least one LED 134 may be configured to produce light within the upper portion 151 and the lower portion 152 of the cavity. The light may pass through the translucent plate 137. The light may further pass through the opening 114, the opening 118, or both, thereby producing ambient lighting around the fragrance dispensing system 100. In an embodiment, the at least one LED 134 includes six LEDs coupled to the controller circuit 138.

The switch connector 135 may be configured to receive the turnable knob 136 and to place the turnable knob in communication with a switch of the controller circuit 138.

For example, the switch connector 135 may be keyed with a star shape that enables an inside of the turnable knob 136 to be press fit to the switch connector 135 and locked into place. The turnable knob 136 may then be rotated to activate different settings of the switch connector 135 and an associated switch coupled to the controller circuit 138.

The translucent plastic plate 137 may cover the at least one LED 134 thereby separating the at least one LED 134 from the lower portion 152 of the cavity. In an embodiment, the translucent plastic plate 137 is cloudy white to modify light from the at least one LED 134 to generate an ambient lighting. Other types of plates are also possible, such as a transparent plate.

The controller circuit 138 may include one or more inputs, switches, processors, and/or circuits capable of initiating operations associated with the fragrance dispensing system 100. An embodiment of the controller circuit 138 is further described with reference to FIG. 2.

The fan 140 may include any type of ventilator system capable of generating an airflow path from the space 150 above the platform to the lower portion 152 of the cavity via the opening 114 of the platform 112 and via the upper portion 151 of the cavity. The airflow path may further pass from the lower portion 152 of the cavity to the space 153 adjacent to the sidewall 116 via the upper portion 151 of the cavity and via the opening 118 of the sidewall 116. To generate the airflow, the fan 140 may use a reverse motion. For example, the fan 140 may be configured to pull air down through the cavity (e.g., from the upper portion 151 to the lower portion 152). In an embodiment, the fan 140 includes two diametrically opposed blades 142, 144. An angle and size of the blades 142, 143 may reduce a noise emitted by the fan while increasing an airflow through the airflow path. In an embodiment, the fan includes three blades. The fan 140 may also be transparent. For example, the fan 140 may be formed of colorless see-through plastic such that light from the LED 134 may pass through the fan 140.

The motor 160 may include any type of motor capable of driving the fan 140. The motor 160 may further include cloth brushing 162. The cloth brushing 162 may reduce an amount of noise and/or vibration associated with operation of the motor 160.

The topper 170 may be configured to fit with the housing 110. When coupled together, the topper 170 and the platform 112 may define an upper cavity configured to retain the EVA bead packet. The topper 170 may include at least one opening 172 defined therein. The at least one opening 172 may enable an air flow path to pass through the EVA bead packet 120 and the at least one opening 114 without being restricted.

During operation, the controller circuit 138 may receive one or more signals indicating an operating state of the fragrance dispensing system 100. Particular embodiments of the operating states of the fragrance dispensing system 100 are described further with reference to FIG. 2. Based on the operating state, the controller circuit 138 may provide electrical power to the motor 160 from the battery 131. The motor 160 may convert the electrical power to mechanical power to drive the fan 140. The fan 140 may cause air to flow in a particular airflow path. For example, the fan 140 may draw airflow in a direction away from the EVA bead packet 120, thereby drawing air from the space 150 above the platform 110 through the EVA bead packet 120 and through the at least one opening 112 into the upper portion 151 of the cavity. An embodiment of the airflow path is further described with reference to FIG. 3. Depending on the operating state, the controller circuit 138 may further provide electrical power to the at least one LED 134.

As further operations, a user may be able to disable the locking mechanism 132 enabling the housing 110 to be separated from the lower module 130. The housing may be replaced by a second housing. For example, the user may prefer a style of the second housing as compared to the housing 110. The second housing may include a second platform configured to receive the EVA bead packet 120. In an embodiment, a plurality of interchangeable housings with different designs may be used with lower module 130.

A benefit associated with the fragrance dispensing system 100 is that the combination of the extended surface area of the EVA beads with the airflow path produced by the fan 140 may enable the fragrance dispensing apparatus to dispense fragrance without heating the EVA beads 122 in contrast to systems that use molded EVA plastic and/or traditional airflow paths. Other advantages and benefits of the fragrance dispensing system 100 will be apparent to persons of ordinary skill in the relevant art having the benefit of this disclosure.

Figure 2:
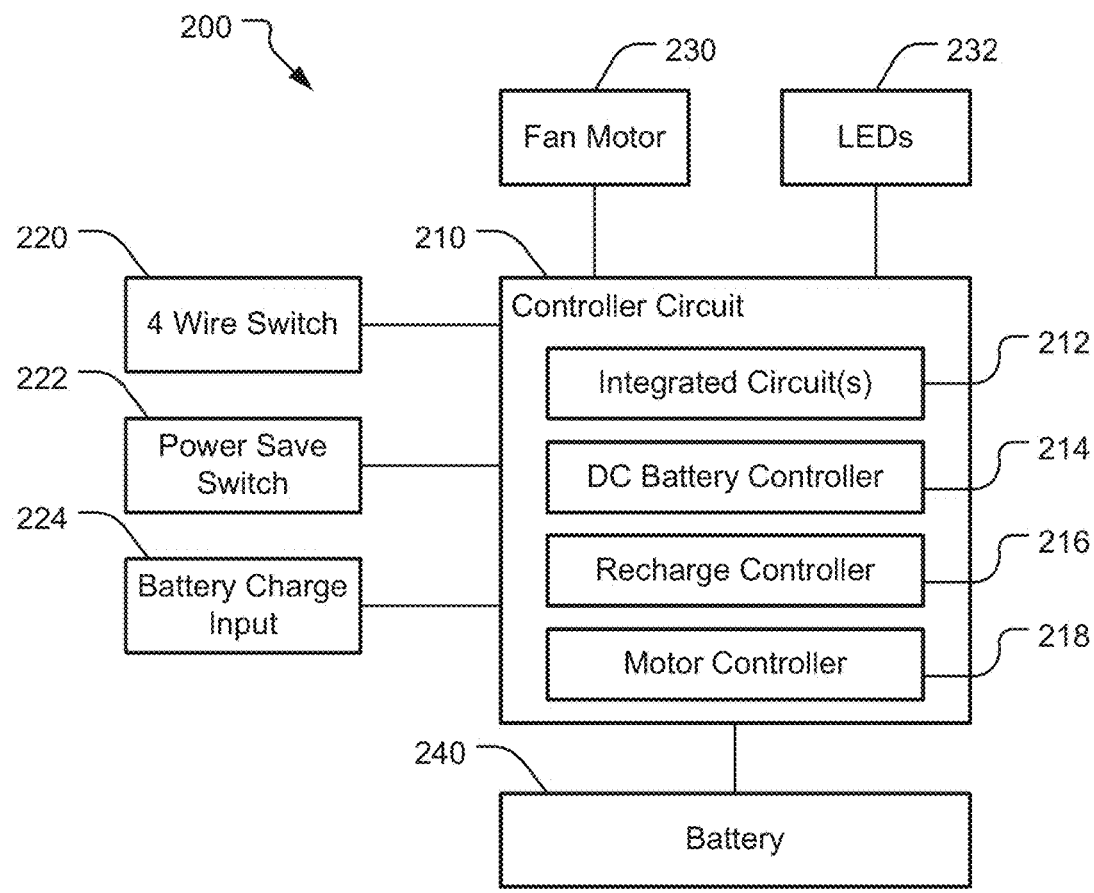
FIG. 2 is a block diagram that depicts an embodiment of a fragrance dispensing system.

Referring to FIG. 2, a block diagram of an embodiment of a system for fragrance dispensing is depicted and generally designated 200. The system 200 may include a controller circuit 210, a four wire switch 220, a power save switch 222, a battery charge input 224, a fan motor 230, at least one LED 232, and a battery 240. The controller circuit 210 may correspond to the controller circuit 138 of FIG. 1, the four wire switch 220 may correspond to and be coupled to the switch connector 135, and the battery charge input 224 may be configured to couple to the recharging cable 133. Further, the fan motor 230 may correspond to the motor 160 and the at least one LED 232 may correspond to the at least one LED 134.

The controller circuit 210 may include one or more integrated circuits 212, a DC battery controller 214, a recharge controller 216, and a motor controller 218. Although, the integrated circuits 212, the DC battery controller 214, the recharge controller 216, and the motor controller 218 are depicted as distinct, in other embodiments, one or more of the integrated circuits 212, the DC battery controller 214, the recharge controller 216, and the motor controller 218, or portions thereof, may be combined.

In an embodiment, the controller circuit 210 includes a printed circuit board (PCB). The PCB may be coupled to the four wire switch 220, the power save switch 222, and the battery charge input 224. The PCB may be further coupled to the integrated circuits 212, the DC battery controller 214, the recharge controller 216, and the motor controller 218. The PCB may also be coupled to the fan 230 and the at least one LED 232.

The integrated circuits 212 may include a processor capable of performing operations associated with the system 200 as described herein. For example, the processor may include any type of processing device such as a central processing unit (CPU), a digital signal processor (DSP), a peripheral interface controller (PIC), and/or another type of processing element.

The DC battery controller 214 may perform operations to selectively operate the battery 240. For example, the DC battery controller 214 may disconnect an output of the battery 240 in response to a determination that the battery has reached a predetermined level of discharge. Further, the DC battery controller 214 may reduce an amount of current drawn from the battery 240 in response to determining that the amount of current exceeds a predetermined threshold. Additionally, the DC battery controller may disconnect an output of the battery 240 in response to an input received from the four wire switch, 220, the power save switch 222, the battery charge input 224, or a combination thereof.

The recharge controller 216 may receive a charging current from the battery charge input 224. Based on the charging current, the recharge controller 216 may generate a charging input usable to charge the battery 240. The charging input may be directed by the recharge controller 216 into the battery 240. Upon detecting that the battery 240 is charged beyond a threshold, the recharge controller 216 may disconnect the charging input from the battery 240.

The motor controller 218 may selectively control the fan motor 230 to adjust a speed of the fan motor 230. For example, the motor controller 218 may receive a signal from the integrated circuits 212 indicating that a speed of the fan motor 230 should be increased or decreased. Based on the signal, the motor controller 218 may increase an amount of power supplied to the fan motor 230.

During operation, the controller circuit 210 may selectively enter an off state, a light state, a low state, or a high state. For example, a user may position the four wire switch 220 to one of four positions corresponding to a particular state. The particular state may be communicated to the integrated circuits 212. The controller circuit 210 may refrain from operating both the fan motor 230 and the one or more LEDs 232 while in the off state. The controller circuit 210 may further refrain from operating the fan motor 230 and may operate the one or more LEDs 232 while in the light only state. The controller circuit 210 may also operate the fan motor 230 at a low speed while in the low state. The controller circuit 210 may operate the fan motor 230 at a high speed while in the high state. Both the high state and the low state may correspond to and be included as part of an on state of the system 200.

The system 200 may further selectively enter a power saving state. For example, a user may position the power save switch 222 to one of two positions indicating to the integrated circuits 212 whether the system 200 is to enter the power saving state. While in the power saving state, the controller circuit 210 may perform power saving operations for a first period of time and may be powered off for a second period of time. To illustrate, the controller circuit 210 may perform power saving operations during 4 hours of a 24 hour period. The power saving operations may include operating the fan for a first duration (e.g., for a 15 minute period) and ceasing to operate the fan for a second duration (e.g., for a 5 minute period). Thus, during the power saving state, the system 200 may conserve power, thereby prolonging an amount of time between battery charges.

A benefit associated with the system 200 including the power save switch 222 is that the system 200 may be more portable as compared to fragrance dispensing systems that do not have power save options. For example, the system 200 may be operated independent of a power input for longer than other systems. In an embodiment, the battery 240 may be able to operate the system 200 for more than 80 hours without being recharged. Other advantages and benefits of the system 200 will be apparent to persons of ordinary skill in the relevant art having the benefit of this disclosure.

Figure 3:
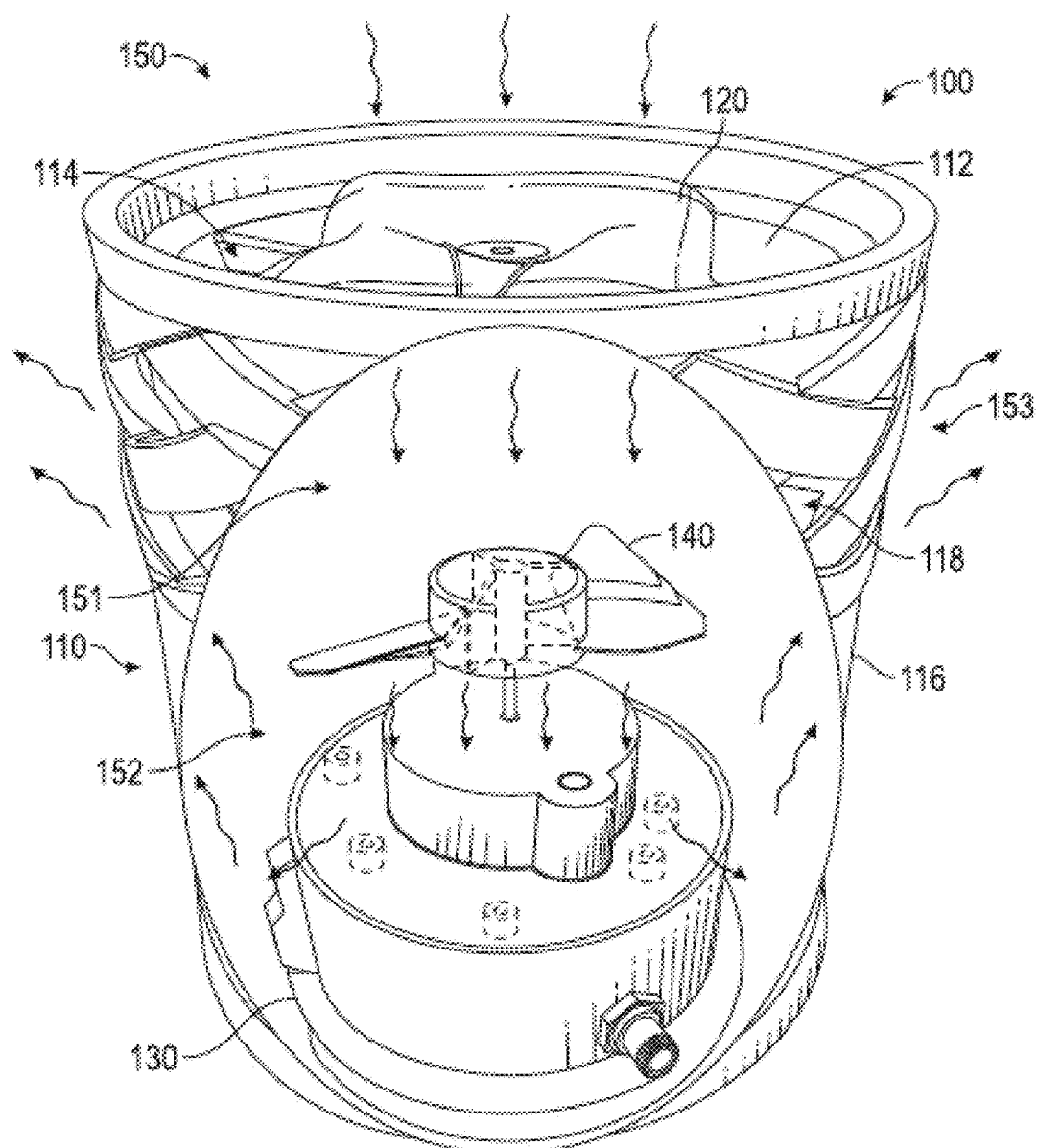
FIG. 3 is a diagram that depicts an embodiment of an air flow path of an embodiment of a fragrance dispensing system.

Referring to FIG. 3, a diagram of an embodiment of an air flow path of an embodiment of the system 100 for fragrance dispensing is depicted. In following the air flow path, air may move from the space 150 above the platform 112 to the upper portion 151 of the cavity via the at least one platform opening 114. In passing through the platform 112, the air flow may further pass through the EVA bead packet 120. In passing through the EVA bead packet 120, the air flow may absorb fragrance from the EVA bead packet 120. The scented air may then flow from the upper portion 151 of the cavity to the lower portion 152 of the cavity due to suction created by the fan 140. The scented air may be compressed in the lower portion 152 of the cavity such that the scented air is forced upward along the sidewall 116 of the housing 110. Hence, the air flow path may pass upward from the lower portion 152 of the cavity to the upper portion 151 of the cavity. From there, the air flow path may pass from the upper portion 151 of the cavity to the space 153 adjacent to the sidewall 116 via the at least one sidewall opening 118. Hence, the system 100 may pull air downward through the EVA bead packet 120 and subsequently force the air outward from the housing 110. Although, FIG. 3 is described in terms of having at least one platform opening 114 and at least one sidewall opening 118, the at least one platform opening 114 may include multiple openings to increase an air flow into the housing 110 and the at least one sidewall opening 118 may include multiple openings to increase an air flow out of the housing 110.

A benefit of the air flow pattern described with reference to FIG. 3 is that an amount of air passing through the EVA bead packet 120 and subsequently passing though the at least one sidewall opening 118 may be greater as compared to systems that do not pull air downward into the lower portion 152 of the cavity. For example, alternate systems may experience less air being directed through the EVA bead packet 120 due to a lack of control over the air flow path. Hence, the system 100 may better disperse fragrance from the EVA bead packet 120 as compared to systems that do not pull air downward and subsequently force the air outward. Other advantages and benefits of the air flow path of the system 100 will be apparent to persons of ordinary skill in the relevant art having the benefit of this disclosure.

Figure 4A:
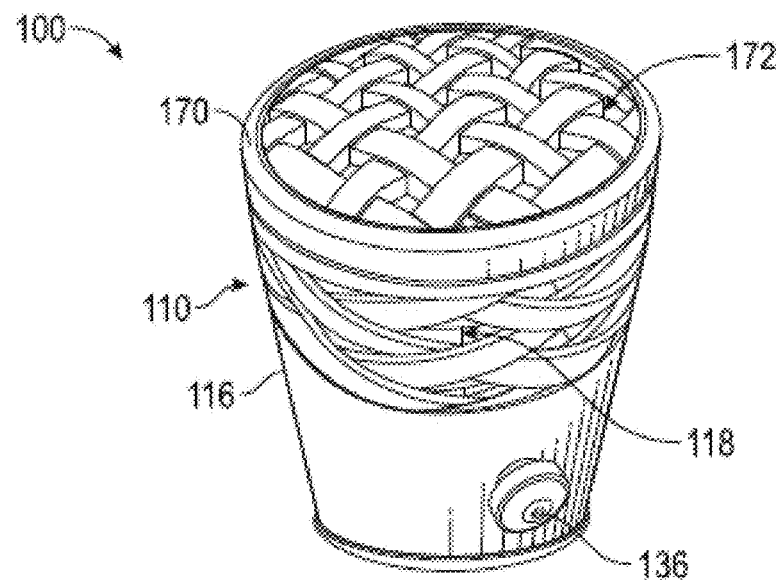
FIG. 4A is a diagram that depicts an embodiment of a fragrance dispensing system including a topper.
Figure 4B:
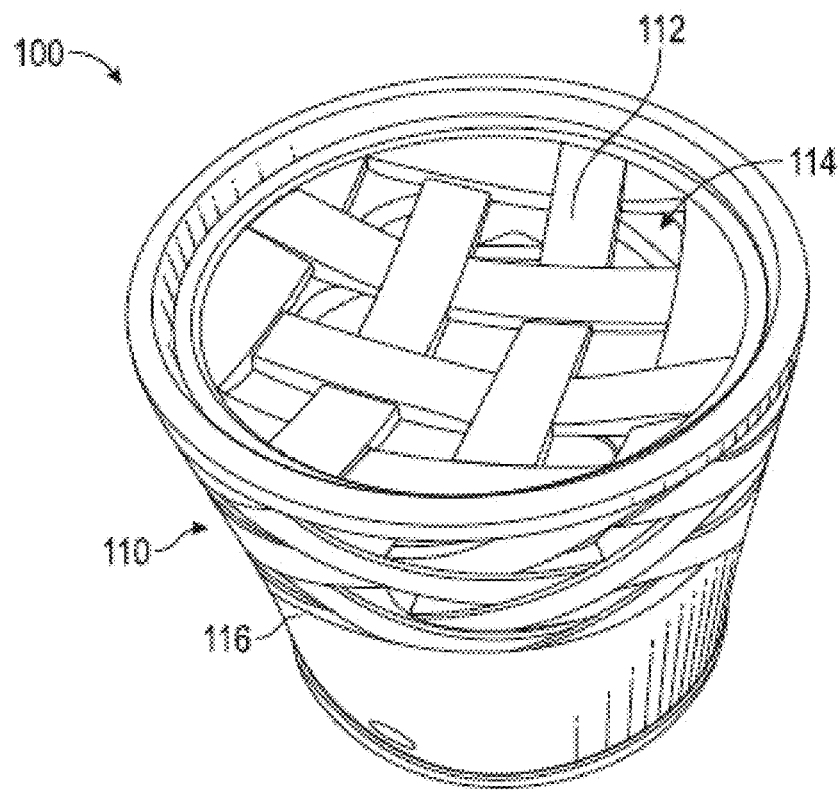
FIG. 4B is a diagram that depicts an embodiment of a fragrance dispensing system with a topper removed.
Figure 4C:
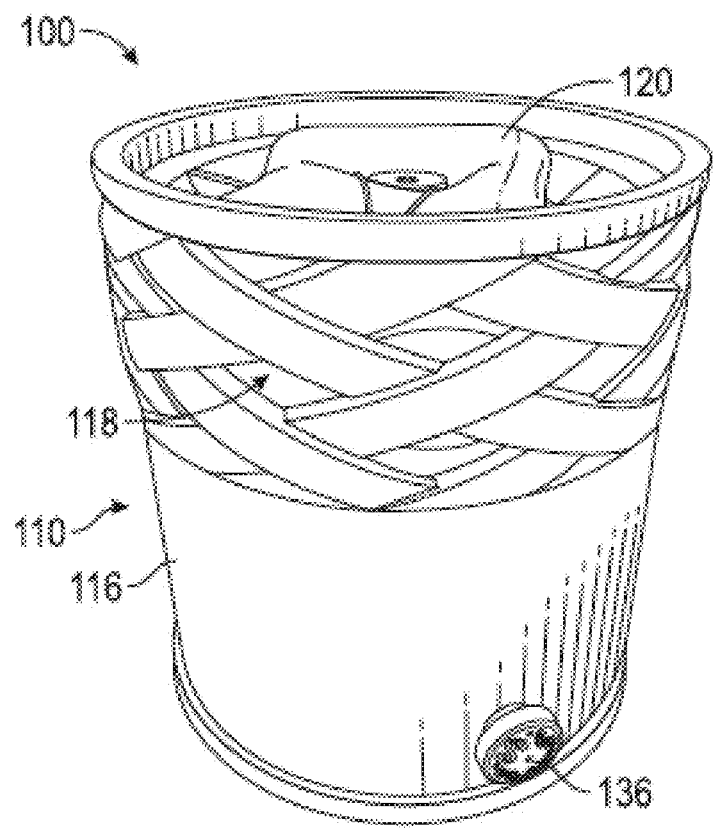
FIG. 4C is a diagram that depicts an embodiment of a fragrance dispensing system that includes an EVA bead packet.

Referring to FIGS. 4A-4C, an embodiment of the fragrance dispensing system 100 is depicted from multiple views. Although FIGS. 4A-4C depict the fragrance dispensing system 100 as including a weaved pattern defining the at least one platform opening 114 and the at least one sidewall opening 118, other embodiments of the fragrance dispensing system 100 may include other designs.

Referring to FIG. 4A, an embodiment of the fragrance dispensing system 100 including the topper 170 is depicted from a top angled view. The topper 170 may include at least one opening 172 defined therein. In an embodiment, the topper 170 includes a plurality of openings defined therein. The collective area of the openings may be greater than or equal to the collective area of platform openings (e.g. the platform opening 114) defined in the platform 112. By having an area that is greater than or equal to the area of the platform openings, the topper 170 may refrain from causing additional air flow resistance to the platform 112. Hence, air may flow freely through the topper 170.

The topper 170 may be coupled to the housing 110 via a press fit mechanism. In other embodiments, other mechanisms may be used to secure the topper 170 to the housing 110. When coupled to the housing 110, the topper 170 and the platform 112 may define a cavity that is configured to retain the EVA bead packet 120.

A benefit of the topper 170 is that the EVA bead packet 120 may be retained securely in place, thereby preventing the EVA bead packet from falling or becoming lost should the fragrance dispensing system be moved or jostled. Other benefits and advantages of the topper 170 will be apparent to persons of ordinary skill in the relevant art having the benefit of this disclosure.

Referring to FIG. 4B, an embodiment of the fragrance dispensing system 100 with the topper 172 removed is depicted from a top angled view. The platform 112 may be concave shaped to better retain the EVA bead packet 120. As depicted in FIG. 4B a plurality of platform openings (e.g., including the platform opening 114) may be defined in the platform 112. Having multiple platform openings may enable the system 100 to have better air flow through the platform 112, and thereby through the EVA bead packet 120, as compared to systems that have relatively few openings. Other benefits and advantages of the platform 112 with platform openings defined therein will be apparent to persons of ordinary skill in the art having the benefit of this disclosure.

Referring to FIG. 4C, an embodiment of the fragrance dispensing system 100 that includes the EVA bead packet 120 is depicted from a side view. The EVA bead packet 120 may be sized to fit over the platform openings 114. When the system 100 is activated (e.g., by the turnable knob 136), fragrance may be drawn from the EVA bead packet 120 downward into the housing 110. The fragrance may then be pushed out through a plurality of sidewall openings (e.g., including the sidewall opening 118) in order to disperse the fragrance through a room. A cumulative area of the sidewall openings may be greater than or equal to a cumulative area of the platform openings, thereby preventing restriction of air flow through the fragrance dispersing system 100. Other benefits and advantages of the sidewall 116 with sidewall openings defined therein will be apparent to persons of ordinary skill in the art having the benefit of this disclosure.

Figure 5:
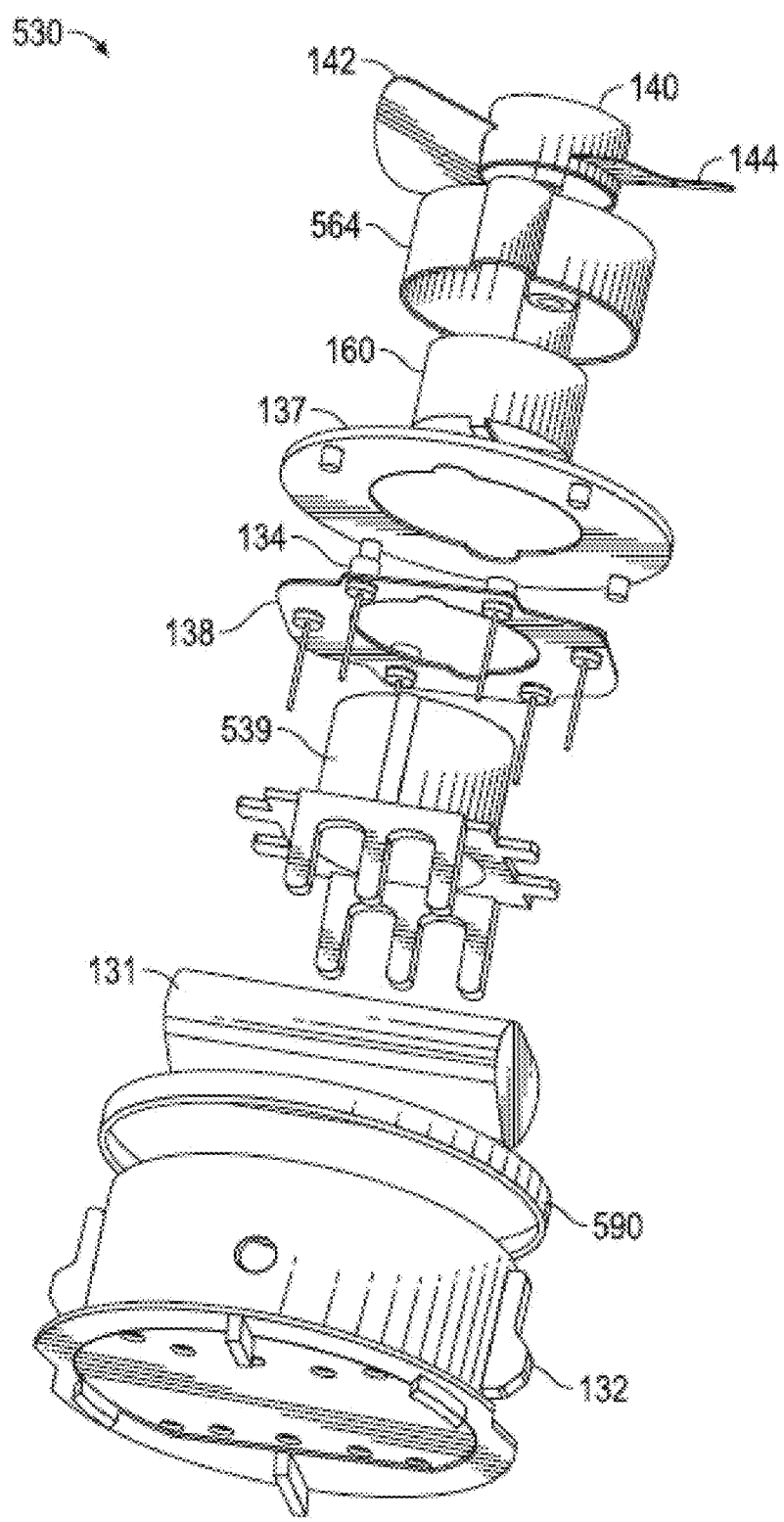
FIG. 5 is an exploded view diagram that depicts an embodiment of a lower module of an embodiment of a fragrance dispensing system.

Referring to FIG. 5, an exploded view of an embodiment of a lower module is depicted and generally designated 530. The lower module 530 may correspond to the lower module 130. For example, the lower module 530 may include the battery 131, the locking mechanism 132, the at least one LED 134, the translucent plastic plate 137, the controller circuit 138, the fan 140, and the motor 160. The lower module 530 may also include an o ring 590, a motor mount 539, and a motor cover 564.

The o ring 590 may help secure a housing (e.g., the housing 110) coupled to the lower module 530. The o ring 590 may further seal the housing (e.g., the housing 110) to the lower module 530, thereby protecting the air flow pattern described with reference to FIG. 3 by preventing air seepage. In an embodiment, the o ring may be a 3 mm thick rubber gasket. The motor mount 539 may be configured to receive and retain the motor 160. The motor mount 539 may further be shaped to substantially retain the battery 131 as well, thereby reducing vibration and noise associated with the lower module 530. The motor cover 564 may include a plastic white motor cover. A non-transparent finish may help modify lighting received by the at least one LED 134 to create ambient lighting. In an embodiment, the motor cover 564 is coupled to the motor mount 539 by screws on either side of the motor cover 564. Other benefits and advantages of the o ring 590, the motor mount 539, and the motor cover 564 will be apparent to persons of ordinary skill in the relevant art having the benefit of this disclosure.

Figure 6A:
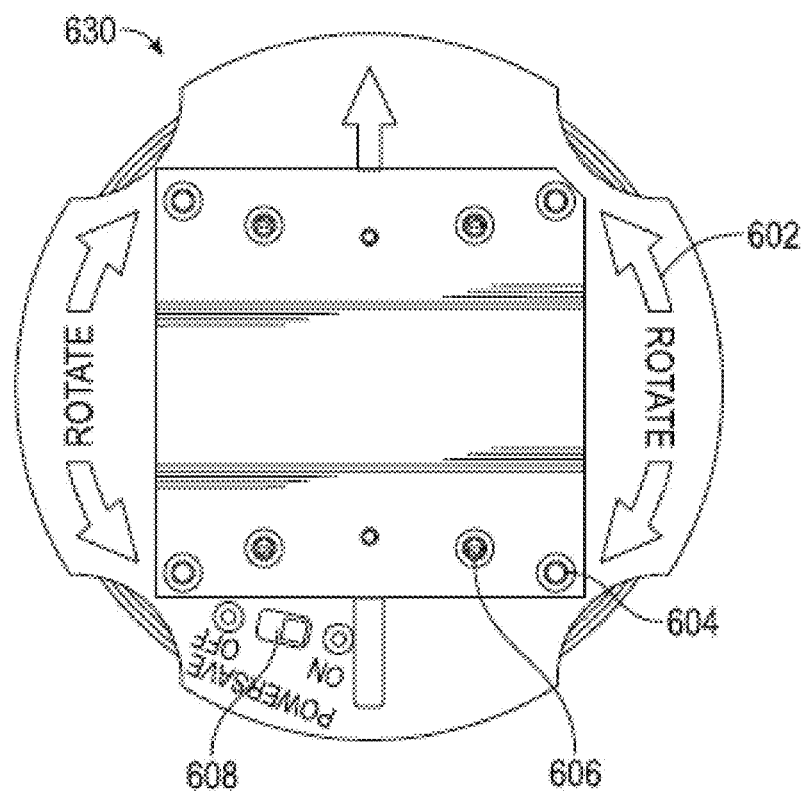
FIG. 6A is a diagram that depicts an embodiment of a lower module including a first embodiment of a locking mechanism.

Referring to FIG. 6A, an embodiment of a lower module 630 including a first embodiment of a locking mechanism is depicted. The lower module 630 may correspond to the lower module 130. The lower module 630 may include a switch 608. The switch 608 may correspond to the power save switch 222 of FIG. 2. The lower module 630 may also include screw holes 604, 606. The screw holes 604 may enable the lower module 630 to couple to the translucent plate 137 and the screw holes 606 may enable the lower module 630 to couple to the motor mount 539.

The lower module 630 may further include molded letters 602. The molded letters 602 may provide instructions to a user for activating the locking mechanism 132. For example, the locking mechanism 132 may be a twisting locking mechanism, and the molded letters 602 may instruct the user to rotate the lower module 630 to lock the lower module 630 to a housing such as the housing 610.

Figure 6B:
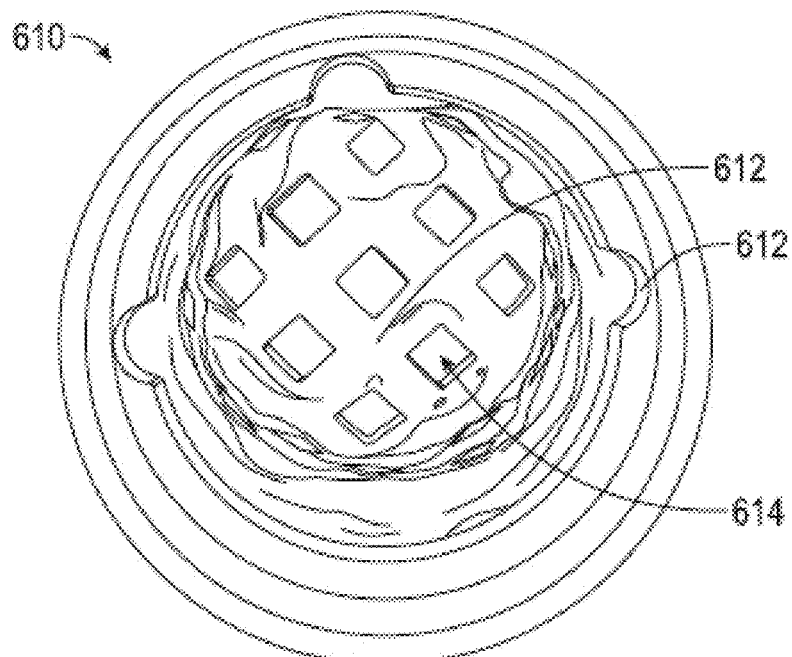
FIG. 6B is a diagram that depicts an embodiment of a housing usable with the first embodiment of the locking mechanism.

Referring to FIG. 6B, an embodiment of a housing 610 usable with the first embodiment of the locking mechanism is depicted. The housing 610 may include at least one half-moon opening 612 defined therein. The at least one half-moon opening may enable the lower module 630 to be inserted into the housing 610 and twisted into place. For example, the lower module 630 may include a notch that fits into the half-moon opening 612. In an embodiment, the half-moon opening 612 fits the switch connector 135 such that the switch connector 135 may be positioned to receive the switch 136 through an opening in the housing 610. The housing 610 may further include additional half-moon openings as depicted in FIG. 6B. In an embodiment, the housing 610 includes three half-moon openings.

A benefit of the twist locking mechanism of FIGS. 6A and 6B is that a user may easily lock and unlock the lower module 630 from the housing 610, thereby enabling the user to easily replace the housing 610 with a second housing of a preferred style. Other benefits and advantages of the twist locking mechanism of FIGS. 6A and 6B will be apparent to persons of ordinary skill in the art having the benefit of this disclosure.

Figure 7:
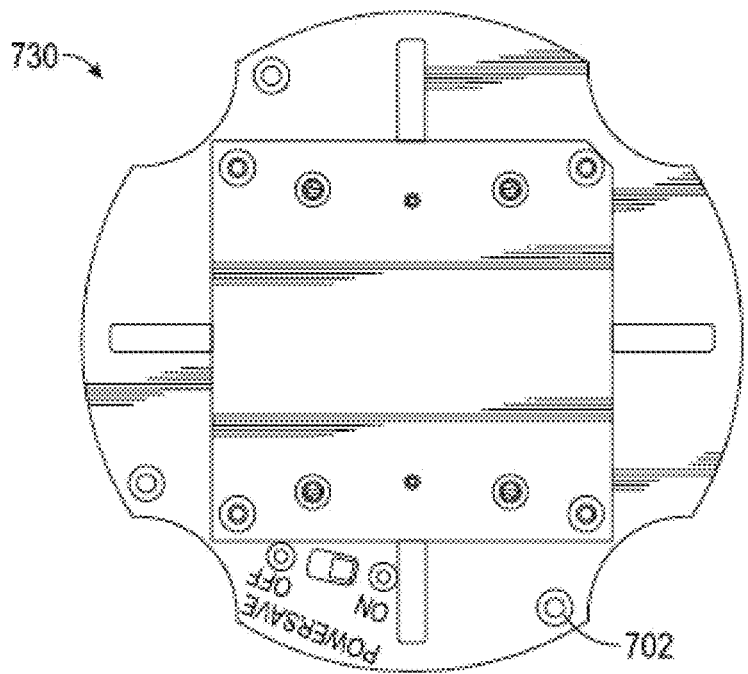
FIG. 7 is a diagram that depicts an embodiment of a lower module including a second embodiment of a locking mechanism.

Referring to FIG. 7, an embodiment of a lower module 730 including a second embodiment of a locking mechanism is depicted. The second locking mechanism may include at least one hole 702 defined within the lower module 730. The at least one hole 702 may be configured to receive a screw therethrough to lock the lower module 730 to a housing (e.g., the housing 110). The second locking mechanism may more securely lock the lower module 730 to a housing as compared to locking mechanisms that do not use screws.

Figure 8:
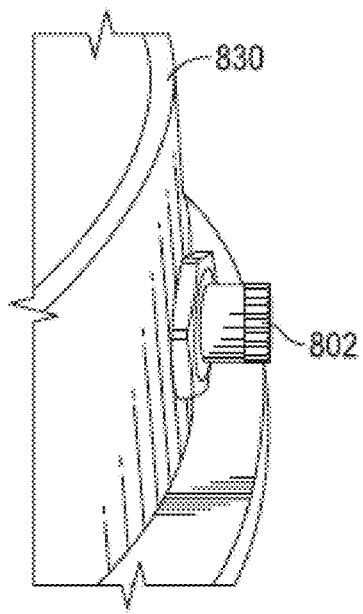
FIG. 8 is a diagram that depicts an embodiment of a lower module that includes a switch mating connector.

Referring to FIG. 8, an embodiment of a lower module 830 that includes a switch mating connector 802 is depicted. The lower module 830 may correspond to the lower module 130. The switch mating connector 802 may correspond to the switch connector 135 and may be keyed with a star shape to enable an inside of a turnable knob to fit tightly to the switch mating connector 802 and to enable the turnable knob to turn a switch (e.g., the four wire switch 220 of FIG. 2) to different settings as described with reference to FIG. 9. Further, the turnable knob may be removed to enable a housing to be removed from the lower module 830.

Figure 9:
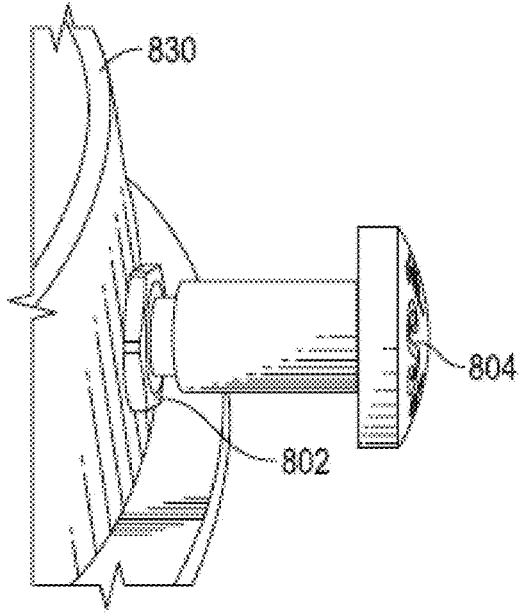
FIG. 9 is a diagram that depicts an embodiment of a lower module with a turnable knob fit onto a switch mating connector.

Referring to FIG. 9, an embodiment of the lower module 830 is depicted with a turnable knob 804 fit onto the switch mating connector 802. By turning the turnable knob 804, a switch may be turned to different settings as described herein.

Referring to FIGS. 10A and 10B, an embodiment of the turnable knob 804 is depicted. FIG. 10A depicts a lower view of the embodiment of the turnable knob 804. An inside 806 of the turnable knob may match the star key of the switch mating connector 802. FIG. 10B depicts an upper view of the embodiment of the turnable knob 804.

Referring to FIG. 11, an embodiment of a method of fragrance dispensing is depicted and generally designated 1100. The method 1100 may include receiving an EVA bead packet at a platform of a fragrance dispensing apparatus, at 1102. For example, the EVA bead packet 120 may be received at the platform 112.

The method 1100 may further include actuating airflow through the EVA bead packet, at 1104. The EVA bead packet may remain substantially unheated by a fragrance dispensing apparatus during actuation of the airflow. For example, the fan 140 may actuate air flow through the EVA bead packet 120, thereby infusing the air with a fragrance received from the EVA bead packet 120 without heating the EVA bead packet 120.

The method 1100 may also include generate an airflow path from a space above a platform to a lower portion of a cavity via the EVA bead packet and via at least one platform opening defined within the platform, from the lower portion of the cavity to an upper portion of the cavity, and from the upper portion of the cavity to a space adjacent to a sidewall via at least one sidewall opening, at 1106. For example, the air flow path described with reference to FIG. 3 may be employed to fill a space with fragrance.

A benefit of the method 1100 is that fragrance may be infused into air passing through the EVA bead packet and may be directed efficiently to a space without heating the EVA bead packet or employing any type of heating element. Other benefits and advantages of the method 1100 will be apparent to persons of ordinary skill in the art having the benefit of this disclosure.

Figure 12:
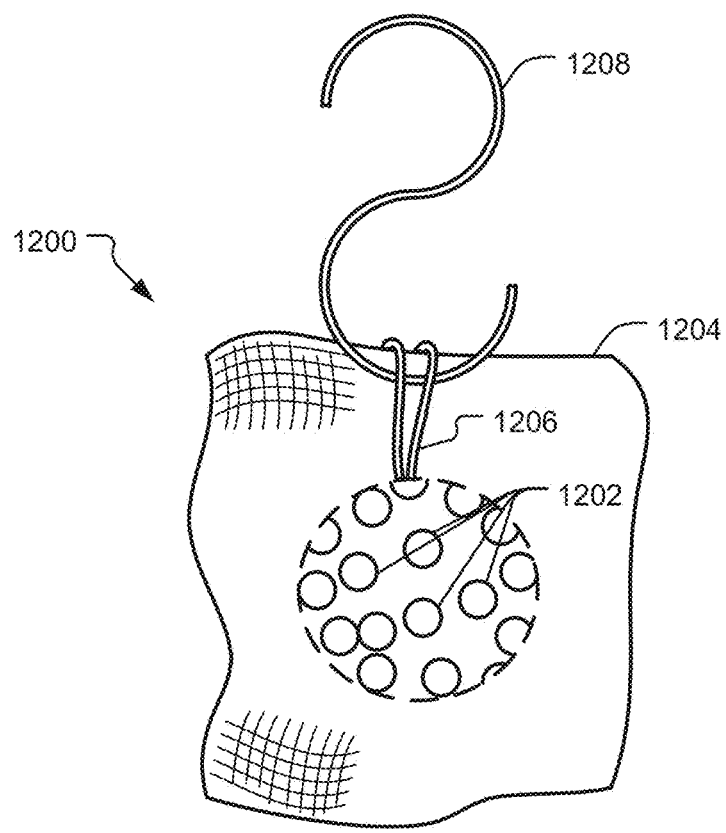
FIG. 12 is a diagram that depicts an embodiment of a bead packet apparatus.

Referring to FIG. 12, an embodiment of a bead packet apparatus is depicted and generally designated 1200. The bead packet 1200 may include a plurality of beads 1202 and a fabric casing 1204. In an embodiment, the bead packet 1200 may have a size and shape that enables the bead packet to fit a platform of a fragrance dispensing apparatus. For example, the bead packet 1200 may correspond to the EVA bead packet 120 and may be usable with the fragrance dispensing apparatus 100.

The plurality of beads 1202 may include EVA beads infused with fragrance. Further, the plurality of beads 1202 may be configured to release the fragrance over a period of time. The fragrance may be released in response to receiving an air flow between the plurality of beads 1202. The amount of fragrance released in response to the air flow may depend on a total surface area of the plurality of beads 1202 that come in contact with the air flow. A total surface area of the plurality of beads 1202 may be sufficiently large to enable a human detectable amount of fragrance to be released. As used herein, a human detectable amount of fragrance is a concentration of scent that enables a typical human to smell the fragrance when located proximate to the bead packet 1200. Different fragrance agents may have different detectability thresholds. Detectability thresholds corresponding to particular fragrance agents are known to persons of ordinary skill in the art. Due to the large surface area that the plurality of beads 1202 present, the human detectable amount of fragrance may be released in the absence of heat above room temperature. As used herein, room temperature means a range of temperatures between 60° F. 100° F. In an embodiment, the plurality of beads 1202 may release a human detectable amount of fragrance at below 75° F. In an embodiment, the beads are infused with a fragrance load of 17 percent. The fragrance load may be an indication of percentage of fragrance agent volume as compared to a volume of fragrance element (e.g., the plurality of fragrance beads 1202).

Particular fragrances that may be infused in the plurality of beads 1102 may include Accord, Amber, Amber Crystals, Aniseed, Apple, Baked Cookie, Bartlett Pear, Basil Leaf, Bergamot, Blackberry, Black Pepper, Blossom, Butterscotch Pudding, Brown Sugar, Caramel, Churned Buttermilk, California Grapefruit, Champagne, Cinnamon, Cinnamon Ceylon, Cinnamon Flower, Cinnamon Sprinkles, Clove, Clove Leaf, Coconut, Cranberries, Creme Fraiche, Crystallized Sugar, Cypress, Dark Amber, Dewy Peach, Fizz Accord, Floral, Fresh Sage, Fresh Vanilla, Geranium, Geranium Rose, Gala Apple, Galbanum, Ginger Root, Golden Delicious, Ground Nutmeg, Honey, Iced Vanilla, Indian Limette, Jasmine, Lemon-Lime, Lime, Mandarin Orange, Mango, Maple, Meyer Lemon, Melted Caramel, Mint, Mixed Fruit, Musk, Myrrh, Nutmeg, Orange, Orange, Orange Flower, Orange Mandarin, Patchouli Leaf, Peach, Pear, Pine, Pineapple, Pine Needle, Prune, Raspberries, Red Raspberries, Ripe Peach, Rum, Salt, Sandalwood, Shaved Ginger, Sizzling Orange, Soft Cinnamon, Spicy, Sugar Plum, Sweet Cinnamon, Sweet Balsam, Tequila, Toffee, Tonka Beans, Vanilla, Vanilla Bean, Vetiver, Warm Toffee, Water Lily, Whipped Butter, Whipped Cream, White Vanilla, Yellow Mandarin, other types of fragrances, or a combination thereof. The particular fragrances listed herein are intended as a non-limiting example. It should be understood that in one or more other embodiments the plurality of beads 1102 may be infused with other types of fragrances not listed herein.

The fabric casing 1204 may include a mesh that enables air flow through the plurality of beads. In an embodiment, the fabric casing 1104 may also include a hook receiver 1206. The hook receiver 1206 may include string or twine coupled to the fabric casing 1104. The hook receiver may be configured to receive a hook 1108, thereby coupling the fabric casing 1104 to the hook 1108.

A benefit of the fragrance packet 1200 may be that the plurality of beads 1202 may release a fragrance without being heated. Further, because the fragrance packet 1200 may be relatively small it may be portable for use in a variety of applications. Also, the hook 1208 may enable the fragrance packet 1200 to be attached to household items, such as a laundry basket, a car mirror, various knobs, etc. Additional advantages and benefits of the fragrance packet 1200 will be apparent to persons of ordinary skill in the relevant art having the benefit of this disclosure.

Figure 13:
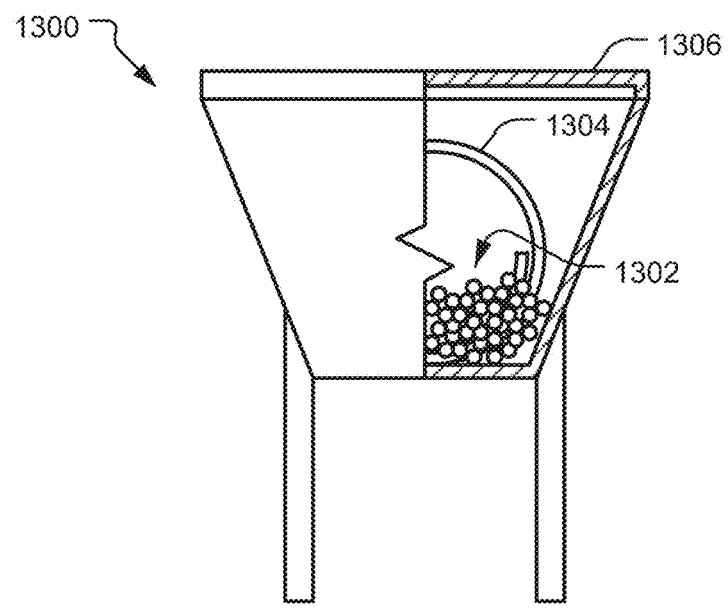
FIG. 13 is a diagram that depicts an embodiment of a tumbler machine.

Referring to FIG. 13, an embodiment of a tumbler machine is depicted and generally designated 1300. The tumbler machine 1300 may be used to tumble a plurality of beads 1302 with one or more fragrance agents. The plurality of beads 1302 may correspond to the plurality of beads 1202.

The tumbler machine 1300 may include a mixing mechanism 1304. For example, the mixing mechanism may include an auger, mixing arm, another mixing element, or any combination thereof. The tumbler machine 1300 may further include a lid 1306. The lid 1306 may be configured to seal the tumbler machine 1300 to prevent fragrance agents from seeping out of the tumbler machine 1300 during tumbling.

Figure 14:
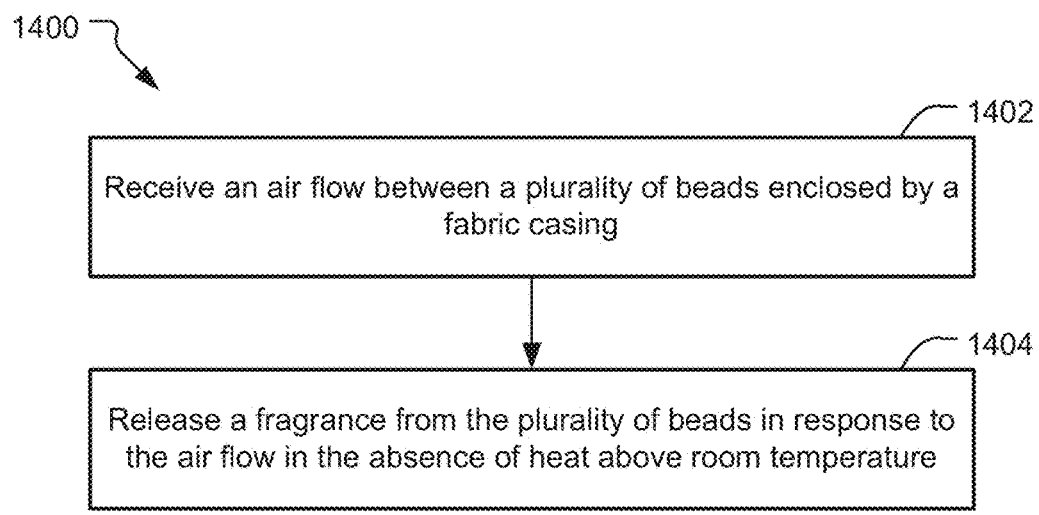
FIG. 14 is a flow chart that depicts an embodiment of a method of dispensing fragrance.

Referring to FIG. 14, an embodiment of a method of dispersing fragrance is depicted and generally designated 1400. The method 1400 may include, receiving an air flow between a plurality of beads enclosed by a fabric casing, at 1402. For example, the plurality of beads 1202 may receive an air flow between the plurality of beads 1202. In an embodiment, the plurality of beads 1202 may include EVA beads.

The method 1400 may also include releasing a fragrance from the plurality of beads in response to the air flow in the absence of heat above room temperature, at 1404. For example, the plurality of beads 1202 may release a fragrance in response to the air flow. As explained herein, the fragrance may be released over a period of time. Further, the fragrance may be released in the absence of additional stimuli such as heat. In an embodiment, the air flow may be generated by a fan, as described with reference to FIGS. 1 and 3.

A benefit associated with the method 1400 may be that the plurality of beads may release fragrance without resorting to using a heating element, thereby making the bead packet safer as compared to fragrance dispensing products that use heating elements. Additional advantages and benefits of the method 1400 will be apparent to persons of ordinary skill in the relevant art having the benefit of this disclosure.

Figure 15:
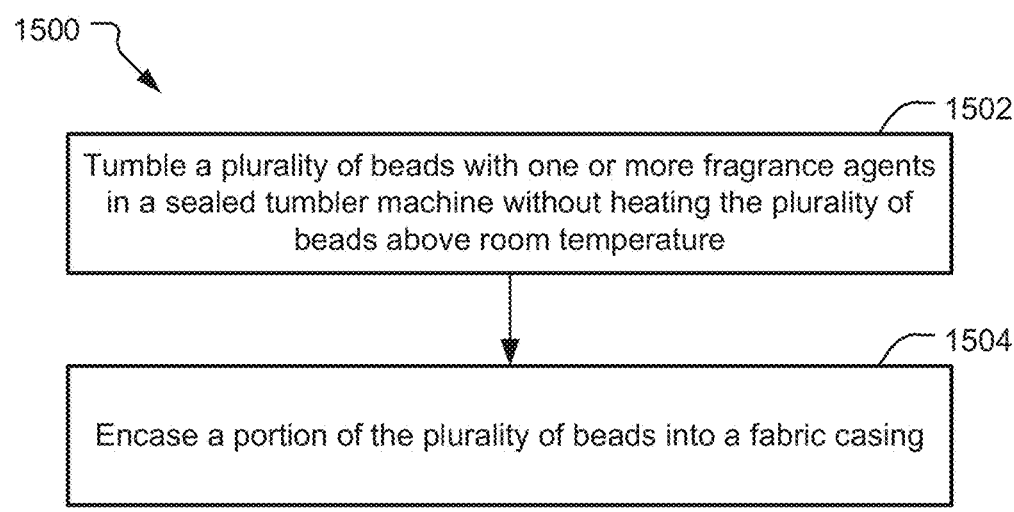
FIG. 15 is a flow chart that depicts an embodiment of a method of manufacturing a bead packet usable with a fragrance dispensing system.

Referring to FIG. 15, an embodiment of a method of manufacturing a bead packet is depicted and generally designated 1500. The method 1500 may include tumbling a plurality of beads with one or more fragrance agents in a sealed tumbler machine without heating the plurality of beads above room temperature, at 1502. For example, the plurality of beads 1302 may be infused with fragrance by tumbling the plurality of beads 1302 in the tumbler machine 1300 with one or more fragrance agents. The tumbler machine 1300 may be sealed by the lid 1306 to prevent the one or more fragrance agents from seeping out of the tumbler machine 1300, thereby strengthening the extent to which the plurality of beads 1302 become infused with a fragrance. The tumbling may be performed for at least an hour for some fragrance agents. Other fragrance agents may require at least three days for the beads to become infused with the fragrance. In an embodiment, the tumbling is performed until the fragrance load of the plurality of beads 1302 is at least 17 percent.

The method 1500 may further include encasing a portion of the plurality of beads into a fabric casing, at 1504. For example, the plurality of beads 1302, or at least a portion thereof, may be encased within a fabric casing (e.g., the fabric casing 1204).

A benefit of the method 1500 is that the beads may be infused with fragrance without being heated as compared to manufacturing methods that do not use a sealed tumbler or that do not use beads which inherently have a high surface area. Additional advantages and benefits of the method 1500 will be apparent to persons of ordinary skill in the relevant art having the benefit of this disclosure.

Although various embodiments have been shown and described, the present disclosure is not so limited and will be understood to include all such modifications and variations are would be apparent to one skilled in the art.

What is claimed is:
1. A fragrance dispensing apparatus comprising:
a housing comprising a platform and at least one sidewall coupled together such that the platform and the sidewall define a cavity, the platform configured to receive an ethylene vinyl acetate (EVA) bead packet, the platform defining one or more platform openings, the one or more platform openings communicatively coupling the cavity to a space above the platform, the at least one sidewall defining one or more sidewall openings, the sidewall openings communicatively coupling the cavity to a space adjacent to the sidewall; and
a lower module comprising a fan having blades that extend from a proximate end to a distal end substantially horizontally, the fan being configured to selectively generate airflow such that air moves from the space above the platform, through the EVA bead packet, through the one or more platform openings, into the cavity, below the fan, up along the sidewall, and through the sidewall openings, the sidewall openings being located between the fan and the platform openings in an elevational direction, the EVA bead packet remaining substantially unheated by the fragrance dispensing apparatus during operation of the fragrance dispensing apparatus.

2. The fragrance dispensing apparatus of claim 1, wherein the fan comprises three blades.

3. The fragrance dispensing apparatus of claim 1, wherein the fan comprises two diametrically opposed blades, wherein an angle of the diametrically opposed blades reduces a noise emitted by the fan while increasing an airflow through the housing.

4. The fragrance dispensing apparatus of claim 1, wherein the fan is transparent.

5. The fragrance dispensing apparatus of claim 1, wherein the lower module further comprises a motor coupled to the fan, the motor including cloth brushing.

6. The fragrance dispensing apparatus of claim 1, further comprising a rechargeable battery.

7. The fragrance dispensing apparatus of claim 6, wherein the rechargeable battery is a high capacity lithium-ion battery capable of operating the fan for at least 80 hours.

8. The fragrance dispensing apparatus of claim 6, further comprising a recharging cable configured to be electrically coupled to the battery.

9. The fragrance dispensing apparatus of claim 1, wherein the lower module further comprises a twist locking mechanism that couples the lower module to the housing when enabled and that releases the housing when disabled, the housing configured to be removed and replaced by a second housing comprising a second platform configured to receive the EVA bead packet.

10. The fragrance dispensing apparatus of claim 9, wherein the twist locking mechanism includes at least one notch attached to a side of the lower module.

11. The fragrance dispensing apparatus of claim 1, wherein the lower module further comprises at least one light emitting diode (LED) configured to illuminate inside the housing and shine through the at least on platform opening, the at least one sidewall opening, or both.

12. The fragrance dispensing apparatus of claim 11, further comprising at least six LEDs, the lower module including a translucent plate separating the at least six LEDs from a cavity defined within the housing.

13. The fragrance dispensing apparatus of claim 1, wherein the lower module further comprises a switch connector configured to receive a turnable knob.

14. The fragrance dispensing apparatus of claim 1, wherein the housing includes ceramic, glass, poly resin, plastic, wood, metal, composites, or a combination thereof.

15. The fragrance dispensing apparatus of claim 1, wherein the housing is configured to receive a topper including at least one topper opening defined therein, wherein the topper and the platform form an upper cavity configured to retain the EVA bead packet.

16. The fragrance dispensing apparatus of claim 1, further comprising the EVA bead packet, the EVA bead packet being at least partially received by the platform.

17. The fragrance dispensing apparatus of claim 1, wherein the platform and the at least one sidewall form a substantially unitary structure, and the platform is curved with an upward-facing concave side.

18. The fragrance dispensing apparatus of claim 1, wherein the sidewall openings are symmetrically located substantially around the entire sidewall.

19. A method of dispensing fragrance comprising:
receiving an EVA bead packet at a platform of a fragrance dispensing apparatus, the platform being coupled with at least one sidewall such that the platform and the at least one sidewall define a cavity, the platform defining one or more platform openings, the one or more platform openings communicatively coupling the cavity to a space above the platform, the at least one sidewall defining one or more sidewall openings, the sidewall openings communicatively coupling the cavity to a space adjacent to the sidewall; and
generating, via a lower module having a fan with blades that extend from a proximate end to a distal end in a substantially horizontal direction, an airflow such that air moves from the space above the platform, through the EVA bead packet, through the one or more platform openings into the cavity, below the fan, up along the sidewall, and through the sidewall openings to the space adjacent to the sidewall,
the sidewall openings being located between the fan and the platform openings in an elevational direction, the EVA bead packet remaining substantially unheated by a fragrance dispensing apparatus during actuation of the airflow.

* * * * *